(12) United States Patent
Guha et al.

(10) Patent No.: US 6,750,466 B2
(45) Date of Patent: Jun. 15, 2004

(54) WEB INSPECTION SYSTEM

(75) Inventors: Sujoy D. Guha, Chula Vista, CA (US); Chris M. Kiraly, San Diego, CA (US); Robin D. Becker, Solana Beach, CA (US)

(73) Assignee: Wintriss Engineering Corporation, San Diego, CA (US)

( * ) Notice: Subject to any disclaimer, the term of this patent is extended or adjusted under 35 U.S.C. 154(b) by 0 days.

(21) Appl. No.: 09/780,313

(22) Filed: Feb. 9, 2001

(65) Prior Publication Data

US 2002/0109112 A1 Aug. 15, 2002

(51) Int. Cl.[7] ................................................. H04N 7/18
(52) U.S. Cl. ............................ 250/559.46; 250/559.44; 356/238.1
(58) Field of Search .................... 250/559.46, 559.4, 250/559.41, 559.42, 549.43, 559.44, 559.45; 356/430, 429, 237.1, 238.1, 238.2

(56) References Cited

U.S. PATENT DOCUMENTS

| | | | | |
|---|---|---|---|---|
| 5,068,799 A | * | 11/1991 | Jarrett, Jr. ................ | 356/238.1 |
| 5,440,648 A | * | 8/1995 | Roberts et al. ............ | 382/141 |
| 5,696,591 A | * | 12/1997 | Bilhorn et al. ............ | 250/559.03 |
| 6,236,429 B1 | * | 5/2001 | Ho ........................... | 348/88 |

* cited by examiner

Primary Examiner—David V. Bruce
Assistant Examiner—Hoon Song
(74) Attorney, Agent, or Firm—Gordon & Rees LLP

(57) ABSTRACT

A web inspection system provides detection of web flaws along the machine direction and cross direction of a web. The detectable percent contrast between good web material and bad web material in one embodiment approaches noise level. The web inspection system utilizes a multiple of smart cameras connected to a host computer via an ethernet hub. Each smart camera includes a line scan camera for producing digital pixels, a means for lighting and pixel correction on a pixel by pixel basis, a web edge detector for monitoring the edges of a web, a multi-pipeline flaw detection preprocessor for detecting very small changes in the web material, a run length encoder for generating data regarding the location of each group of potential flaws in a cross direction, a 2D blob detector and analyzer for generating data regarding the location of block flaws along a machine direction, and an inspect/reject analysis for determining the actual flaw data from the potential flaw data. A low contrast web inspection system provides a balanced and distributed architecture that handles high defect rates, and that is easily integrated with an existing web manufacturing system.

11 Claims, 10 Drawing Sheets

FIG. 8

WEB INSPECTION SYSTEM

BACKGROUND OF THE INVENTION

1. Field of Invention

The present invention relates generally to web inspection systems and more specifically to smart camera systems for detecting flaws and defects of web material.

2. Background

A "web" is a flat material produced continuously in large quantities and at very high rates. Typical web materiel includes fabrics, sheet metal, paper, and non-woven plastic, etc. Inspection of the web material surface is required during production to find flaws and defects. Failure to detect these flaws and defects may result in thousands of feet of unusable web material. Thus, there exists varying methods of web inspection from manual inspection and sampling to image acquisition, processing and analysis.

FIG. 1 illustrates a traditional system 10 for web inspection utilizing line scan cameras 22 positioned above a web 12. Typically, two types of sensor technology, charge coupled device (CCD) or CMOS, are utilized. While CMOS technology allows the signal processing electronics to be on the same chip as the sensor, CCD sensor technology offers advantages superior imaging quality as compared to CMOS sensors, and stand alone components. Continuing with FIG. 1, high bandwidth camera-specific data cables 34 are required to transfer data from the line scan cameras 22 to a vision processor 32. A typical high bandwidth data stream transfer is forty (40) million pixels per seconds, i.e., 500 Mbits per second for pixels of eight (8) bits.

The megapixel data stream is transferred over the camera-specific cables 34 to frame grabber modules 24 in the vision processor 32. Frame grabber modules 24 utilize standard integrated circuit (IC) boards to digitize an analog video stream image from a line scan camera 22. The digitized images, represented by arrays of numbers, are streamed to pipeline vision processors 26 for real time preprocessing. The pipeline vision processors 26 utilize dedicated image processing boards for data and image analysis that may be different for various webs. For example, a pipeline vision processor 26 may be configured to extract specific information from an image. The processed images from each of the pipeline vision processors 26 are sent to an image analyzer processor 28 that further analyzes and processes an image of the full width of the web 12. The web inspection system 10 of the prior art may further include an image buffer board 30 for data storage. The vision processor 32 of the prior art requires a large chassis to house the IC boards of the frame grabber modules 24, the pipeline vision processors 26 the image analyzer processor, and the image buffer 30.

The processed image from the vision processor 26 is sent to a host computer 14 for display on the graphical user interface (GUI) of the host computer 14. Also connected to the host computer 14, is a defect marker 18 and an encoder 16. The encoder 16 sends information to the host computer 14 including the speed of the web 12. The web 12 typically moves over a rotary device driven by a shaft and roller that produce pulses per unit distance. The host computer 14 utilizes this information to determine the size and position of a defect. The host computer 14 may also include a database input/output board to control a defect marking system 18, and other peripheral device connections 20.

The web inspection systems 10 of the prior art present several disadvantages. As described above, prior art web inspection systems 10 require a high number of components that are supplied by many different manufacturers, thus presenting compatibility problems. Integration of the components is difficult and expensive, and the resulting system is often difficult to configure and use. The prior art web inspection systems 10 typically have large footprints and require racks or large custom boxes of boards for parallel processing. These extra racks of equipment and the operator console, or host computer 14, must be out on the floor and relatively close to the web equipment 12 due to the constraints on the length of connecting cables which must transmit a large bandwidth of data. For example, custom shielded cables are required to connect components to protect the video signal from picking up background noise. The requirement of proprietary cables and the large bandwidth transmission of the high speed raw image data from the cameras limits and/or preempts the use of standard factory ethernet cables to link all components and factory computers.

A further disadvantage of the prior art web inspection systems 10 as shown in FIG. 1 is the low mean time between failure due to the number of components. In addition, a web inspection system 10, as shown in FIG. 1, is an unbalanced architecture, meaning that one component in the system often limits the performance of the system. For example, high speed data sent over cables 34 may jam processing in the vision processing box 32. Also, high defect rates may cause overload occurrences in the image analyzer processor 28. Expansion of an unbalance architecture to add more capability is usually very expensive, and the system 10 is often already maximized, e.g. the rack holding the equipment cannot accept more boards. Another drawback of the non-robust web inspection system 10 of the prior art is that the system 10 is not easily scalable. Therefore, if a customer requires the detection of defects that are half the size that the current system 10 is capable of detecting, more cameras may be added, but the system 10 cannot be configured to accept more pipeline vision processors 26 and/or a second image analyzer 28.

Thus there exists a need for a balanced and robust web inspection system that is easily integrated with an existing manufacturing Ethernet, and is capable of detecting a high rate of web flaws and defects.

SUMMARY OF THE INVENTION

It is an advantage of the present invention to provide smart cameras for processing images at the front end of the system to limit the bandwidth required to transmit image data.

It is a further advantage of the present invention to provide a robust web inspection system that is capable of expansion.

It is another advantage of the present invention to provide a web inspection system that may be connected to an existing factory ethernet.

It is yet another advantage of the present invention to provide a web inspection system that can be readily expanded as required.

It is yet another advantage to provide a low contrast web inspection system that is capable of detecting flaws and defects in web material that are close to the noise level.

Still another advantage of the present invention is to provide a web inspection system that requires a limited number of components thus increasing the mean time between failure of the web inspection system.

The present invention also provides a balanced architecture for processing data that results in predictable response and more robust behavior.

In an exemplary embodiment of the present invention, a web inspection system includes at least one smart camera for generating digitized images of portions of a web material having a flaw or defect. Each smart camera is connected via an ethernet hub to a host computer. The host computer and a web encoder monitor the web speed and send control signals to the each smart camera. Each smart camera is connected to a marking system for marking the web proximate to each flaw or defect with corresponding codes or other markings. In an exemplary embodiment each smart camera includes a head board for capturing an image of a portion of a web, and digitizing the image, a processor for analyzing the image, an input/output board for controlling the input and output of the image data signals, and a power supply board for supplying the smart camera components with required voltages.

In an exemplary embodiment of the present invention, the smart camera is capable of detecting very small flaws and defects of the web, i.e. the contrast between a flaw and good web material is close to a noise level. The smart camera of the exemplary embodiment includes all signal processing devices, and only web flaw information and flaw images are sent to the host computer. However, the smart camera is capable of sending any portion of the real-time web image during periods of low bandwidth usage, e.g. when the number of web flaws is minimal.

The smart camera of the exemplary embodiment includes a line scan camera, a lighting uniformity correction and pixel sensitivity correction circuit, a web edge detector circuit, a multi-pipeline flaw detection pre-processor, a run length encoder, a two dimensional blob detector circuit, a two dimensional blob analyzer, and an inspect/reject criteria analyzer. The line scan camera supplies a digital video stream of the web to the lighting uniformity correction and pixel sensitivity correction circuit. Each pixel of the digital video stream is corrected or adjusted according to a pre-determined baseline. The web edge detector determines the location of the edge of the web, and transmits the web edge data and corrected digital video stream to the multi-pipeline flaw detection preprocessor.

The multi-pipeline flaw detection pre-processor of an exemplary embodiment includes programmable two dimensional filters including a background filter, a machine direction streak filter, a cross direction streak filter, and a small flaw filter. Each filter determines an average pixel value along a portion of the web. The average pixel value, which is constantly updated, becomes a reference for an adjacent portion of the web. The multi-pipeline flaw detection pre-processor also includes four adaptive background subtraction channels that subtract the averaged background from the corrected digital video stream, the output of the machine direction streak filter, the output of the cross direction streak filter, and the output of the small flaw filter. In the exemplary embodiment, four multi-group thresholders group pixels for each adaptive background subtraction channel. The four multi-group thresholders include a single pixel flaw detector, a machine direction streak detector, a cross direction streak detector, and a small flaw detector. A fifth multi-group thresholder uniformity detector groups pixels for the output of the background filter. The outputs of the multi-group thresholders are video signals that include potential web flaw data. These signals are sent to a priority logic circuit of the multi-pipeline flaw detection pre-processor to prioritize the signals according to programmable thresholds and rules.

The prioritized signal from the multi-pipeline flaw detection pre-processor is sent to a run line encoder to determine the start and stop pixels for the detected web flaws. A two dimensional blob detector and analyzer perform a connectivity analysis on the continuous stream of prioritized signals to determine whether groups from a same flaw class touch to form blobs, i.e. two dimensional areas of flaw. The resulting output data from the blob analyzer and the prioritized signal is then analyzed by a programmable inspect/reject criteria to determine whether the detected blobs rise to the level of a flaw. The output from the inspect/reject criteria analysis, which includes video and control data, is output from the smart camera to the host computer.

In the exemplary embodiment of the present invention, the host computer records and displays the flaw information, including an image, location information, and the class of the flaw. The host computer may also request real-time video of the web as permitted by the availability of system bandwidth. The host computer of the exemplary embodiment performs trend analysis on the detected web flaws to determine whether any particular web flaw is occurring at a regular interval at a same location on the web. The detection of a regularly occurring flaws may indicate specific problems with the web manufacturing equipment.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which:

FIG. 6b is a block diagram of the multi-pipeline flaw detection pre processing block of the low contrast web inspection system of FIG. 6a;

FIG. 8 is an illustration of a web monitoring graphic user interface of the present invention;

DESCRIPTION OF THE PREFERRED EMBODIMENT

Figure 1:
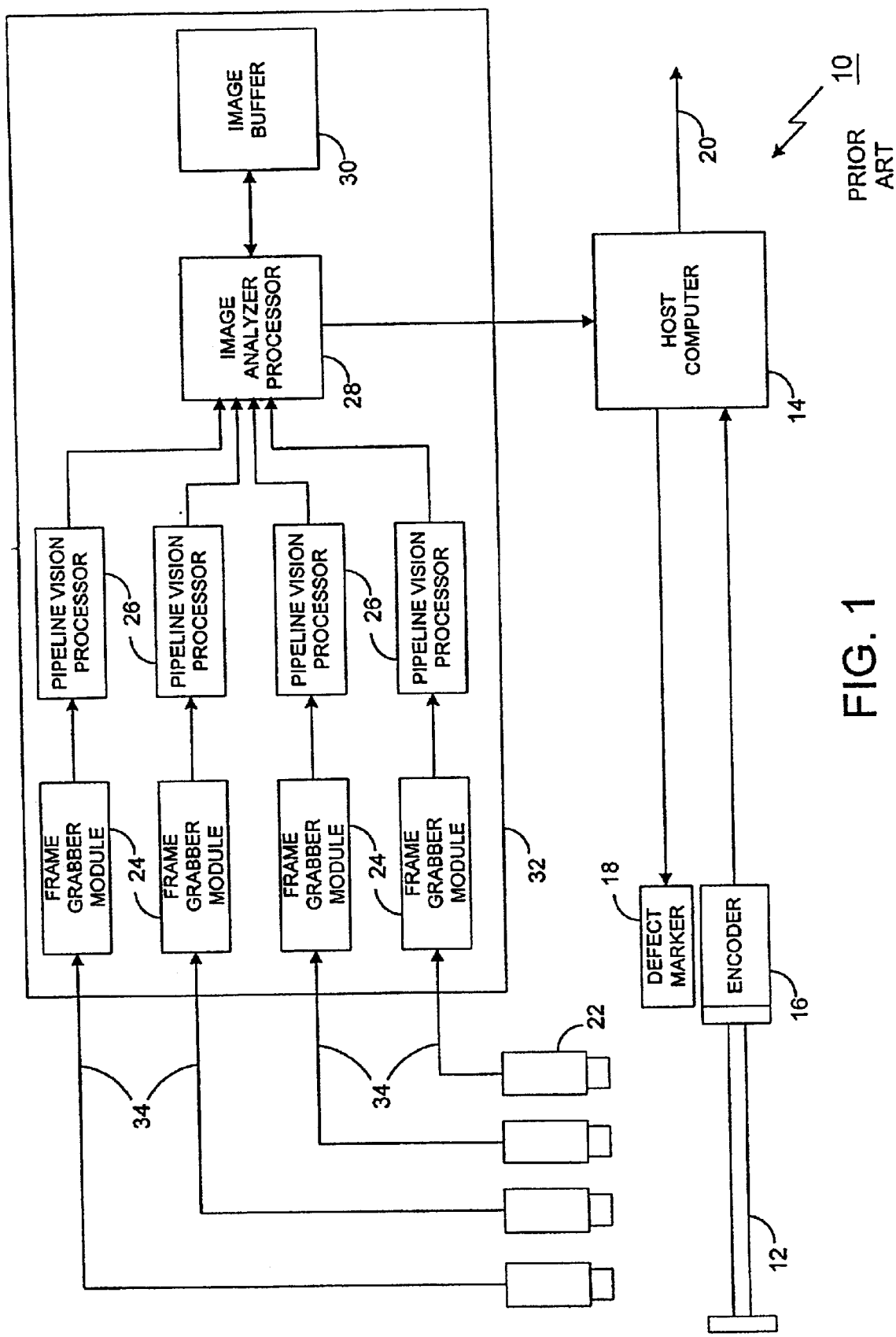
FIG. 1 is a block diagram of the traditional prior art web inspection system.
Figure 2:
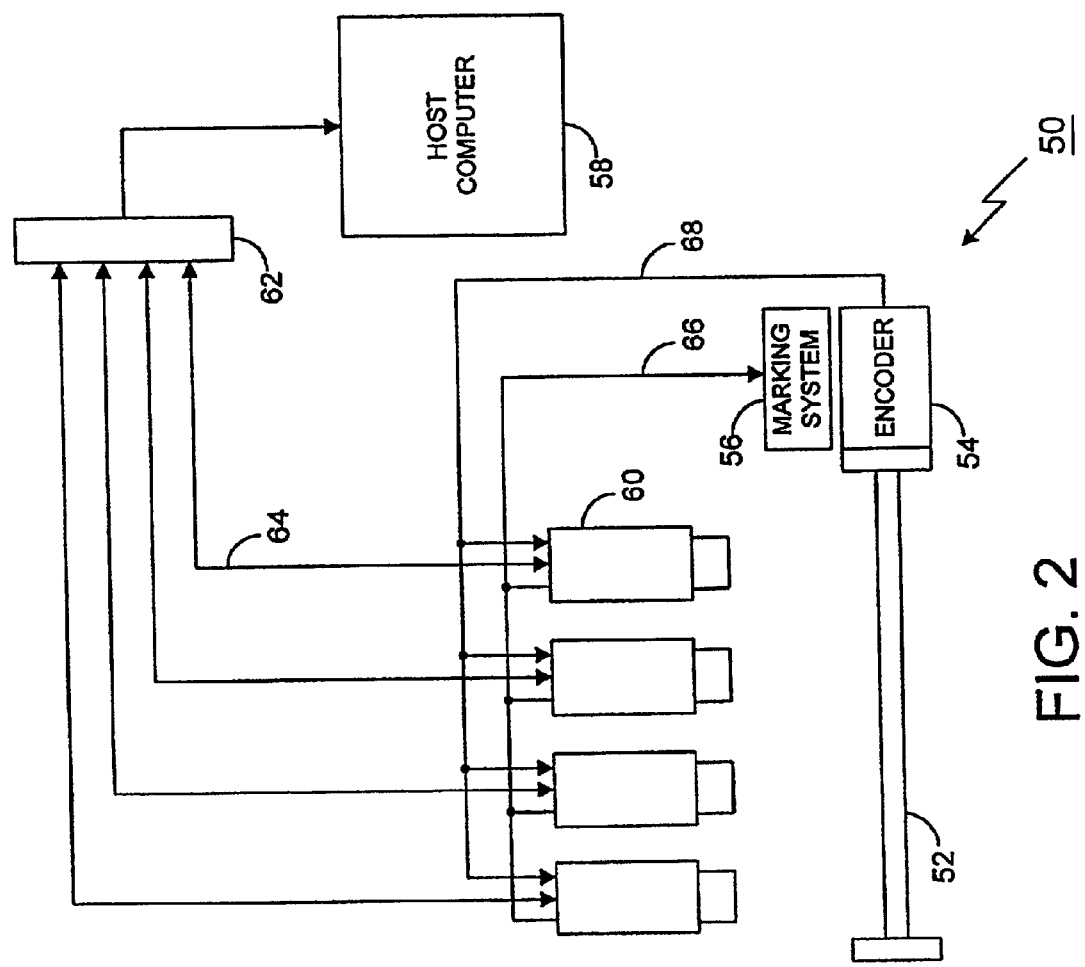
FIG. 2 is a smart camera web inspection system of the present invention.

FIG. 2 illustrates a smart camera approach to a web inspection system 50 of a preferred embodiment of the present invention. The web inspection system 50 includes smart camera systems 60 for monitoring a web 52. Each smart camera 60 is connected to a host computer 58 through an ethernet hub 62 utilizing standard ethernet cabling 64. The ethernet cabling 64 includes control lines for delivering control signals to the smart cameras 60 from the host computer 58, and image lines for sending defect images and information to the host computer 58. Each smart camera 60 receives real-time control and synchronizing signals 68 from a web encoder 54 that monitors the speed and position of the web 52. The information from the web encoder 54 allows the smart cameras 60 to track the position of a defect along the length, or machine direction (MD), of the web. Control signals from the encoder ensure that the smart cameras 60 are synchronized in real time, and thus, provide synchronized images to the host computer 58. The position of a defect along the width, or cross direction (CD), of the web 52 is known by the identity of the camera 60 sending the defect information. A marking system 56 for marking the web 52 receives control signals from each smart camera 60 on a third control line 66. The third control line 66 is one of a set of general input/output control line that also may be utilized for receiving switch signal inputs, e.g. cut controls that signal when the web 52 will be cut. The configuration of the web inspection system 50 of FIG. 1 may be expanded by the addition of smart cameras 60.

Figure 10:
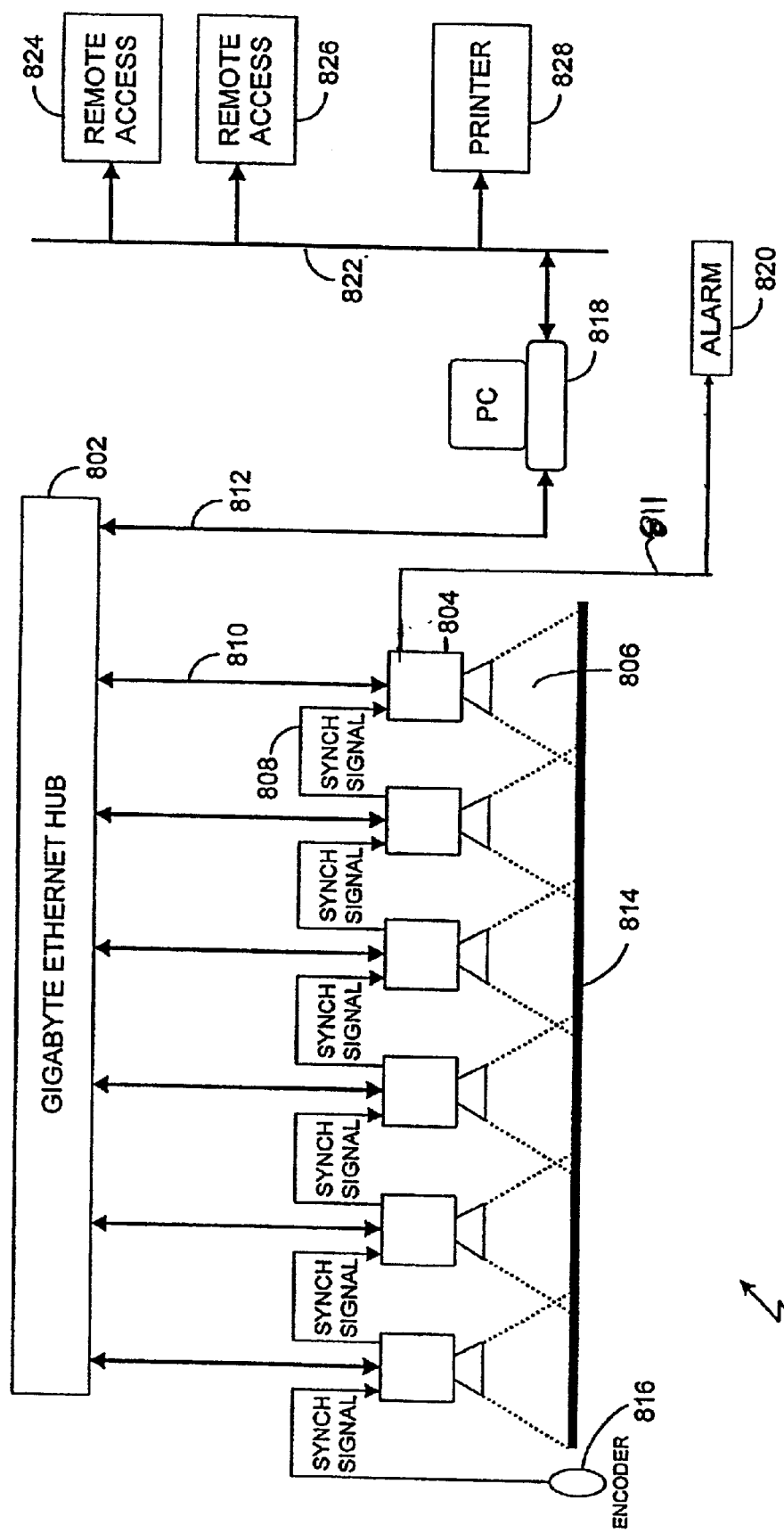
FIG. 10 is a block diagram of a factory web inspection system.

FIG. 10 illustrates an embodiment of the smart camera web inspection system 800 of the present invention integrated with a factory net 822. Each smart camera 804 monitors a section 806 of the web 814. Any number of smart cameras 804 may be connected and synchronized via a control signal 808 from an encoder 816 monitoring the speed of the web 814. The control signal from the encoder 816 is utilized by the smart camera 804 to determine the position of a detected flaw or defect on the portion of the web 806 that is monitored by the smart camera 804. Each smart camera 804 is connected via standard ethernet cabling 810 to an ethernet hub 802. One of the nodes 812 on the ethernet hub 802 is a personal computer 818 having an operator interface that provides a control and monitoring means for the web inspection system 800. The web inspection system 800 is further connected to the factory network 822 for remote access 824, 826 and for printing reports 828. Devices such as alarms 820 may be connected to a control line 811 to provide automatic means for notifying the operator of flaws or defects that exceed a predetermined threshold.

Referring to FIG. 2, the smart camera system of the present invention 50 integrates an acquisition sensor of the camera 22 or frame grabber module 24, a pipeline preprocessor 26, and an image analyzer processor 28 of the prior art into a single smart camera box 60. Required bandwidth is minimized since only detected flaws and defects of the inspection and corresponding flaw position information are communicated to the host computer 58 through ethernet outputs 64 to an ethernet hub 62. Thus, off-the-shell ethernet cables 64 may be utilized between the smart cameras 60 of the present invention and an ethernet hub 62.

The smart camera web inspection system 50 of FIG. 2 has additional advantages over the prior art system of FIG. 1. The lower number of components of the smart camera web inspection system 50 requires less factory floor space. In addition, all vision components are contained within a smart camera box 60, and are provided by single manufacturer thus alleviating compatibility, integration, and set-up problems. Because only flaw and defect information and images are sent to the host computer 58, the system bandwidth is not likely to be exceeded, and access to the flaw or defect data during system operation does not degrade system performance. Another advantage of the smart camera web inspection system 50 of the present invention is that more cameras 60 may be added to the system 50 without causing bottleneck problems on the ethernet 62, or at the host computer 58 which displays and processes the incoming flaw and defect data. The addition of cameras 60 does not require addition of pipeline vision processor circuit cards or image analyzer processors and the associated rack equipment as required by prior art configurations.

Another advantage of the present invention is that the operator console, or host computer 58, may be located in any convenient location on the manufacturing floor since the length of the standard cables 64 do not have to be limited. Also, the reduced number of components of the web inspection system 50 of the present invention eliminates the need for computer interrupts, memory chip sets, and/or input/output conflicts that are associated with the use of extra integrated circuit boards and other components.

Figure 3:
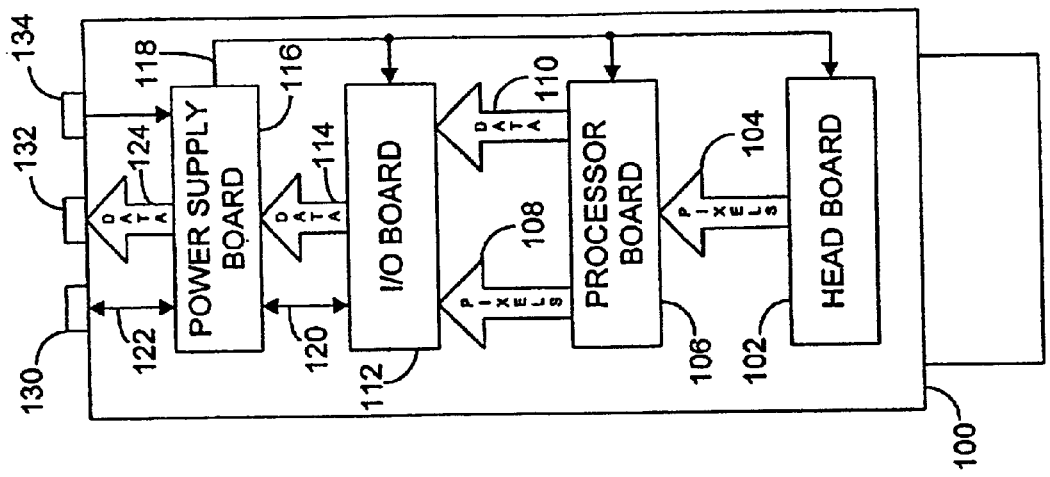
FIG. 3 is a block diagram of a preferred embodiment of a smart camera of the present invention.

FIG. 3 illustrates a camera 100 hardware solution of the preferred embodiment for a web inspection system 50 as shown in FIG. 2. A head board 102 continuously captures images of the web and sends a pixel signal 104 to a processor board 106. The head board sensor of the preferred embodiment has 5150 maskable pixels to generate an image at an instant in time, and generates up to 40 million pixels per second. Each image is digitized and light corrected on the head board 102, and the digitized pixels 104 are sent to the processor board 106 for flaw detection. Pixels for detected flaws 108, as well as corresponding flaw data 110, is sent to the input/output board 112. The input/output board 112 further processes the data for transmission to the host computer. The defect image data 114, 124 is sent to a host computer via an output connection 132 over an ethernet cable. The I/O board 112 also receives/sends control information from/to an external device via control lines 120, 122 connected to a control connector 130. A power supply board receives at least one supply voltage via a power connector 134, and converts the supply power to appropriate voltages 118 utilized by the camera 100 components. In other embodiments of the camera 100, data 114 and control information 120 is connected directly to the connectors 130, 132.

Digitization of the web image inside the camera 100 provides zero pixel jitter, low noise, and no electronic aliasing. In prior art systems, a camera sensor senses each pixel element and outputs an analog signal. Because it is not obvious where each pixel starts and stops, a pulse must be utilized to indicate where a pixel line starts. Thus, if a small amount of skew of the sample or pulse occurs as a result of sending the analog signal down a cable, a processor may not be able to distinguish each pixel correctly, which causes jitter of the analog pixel data. In the present invention, the head board 102 captures the analog pixel signal 104, and digitizes them. In an alternate embodiment, the head board sends an analog pixel signal 104 to the processor board 106. Since the digitizing takes place on the head board 102, there is little or no jitter.

The camera 100 of the present invention also significantly reduces electronic aliasing, which is the "fuzziness" associated with a display of an image that occurs when insufficient data bits are available to represent each pixel. For example, a raw signal of an alternating black and white image has abrupt transitions. To gate a square wave in a digitizer on the other end of a cable, four times the bandwidth is needed to sample the signal. Depending on the flaw rate of the web, the volume of data that must be exchanged between the components of the prior art system may overload the system. Minimizing the amount of processed data reduces the resolution of the image of the web. The present invention greatly reduces the volume of data because the web image data is processed in the camera, and only flaw or defect data is sent across the ethernet cable. For example, in the present invention, if a single flaw is represented by 4 kilo bytes, and one flaw per second is detected, then only 4 thousand bytes of data per second are transferred to the host computer 58. The prior art systems are required to send the entire web image, which may be up to four orders greater in magnitude of data than the system of the present invention. For high web flaw rates, i.e., for increasing web flow speeds, the number of bits of data transmitted over the ethernet increases for the systems of both the prior art and the present invention. However, limiting data transmissions to flaws and defects and associated data, allows the use of standard cables in the preferred embodiment of the present invention.

There are several web inspection categories including high contrast, medium contrast and low contrast web inspection, so named based upon the level of detectable contrast between the good material and bad material as compared to the web material color variation. In a high contrast web inspection system, the cameras are typically able to detect contrast variations of 6 percent or more from the standard material (global color). A high contrast web inspection system may be utilized for applications such as the detection of pinholes in plastic, scratches on metal, and bright or dark marks on rubber. A medium contrast web inspection system has a capability of detecting defects that have a 6 percent contrast difference from the local color variation of the web. The medium contrast web inspection system is capable of detecting defects in the presence of changing circumstances, e.g., scratches on metallic surfaces in the presence of normal variations in texture. A low contrast web inspection is capable of detecting defects and flaws with a contrast very close to the noise level of the signal. The low contrast web inspection system may be utilized for applications requiring detection of holes, streaks, or clumps in porous material and faint scratches on flat surfaces or the presence of normal variations in textures.

Figure 4:
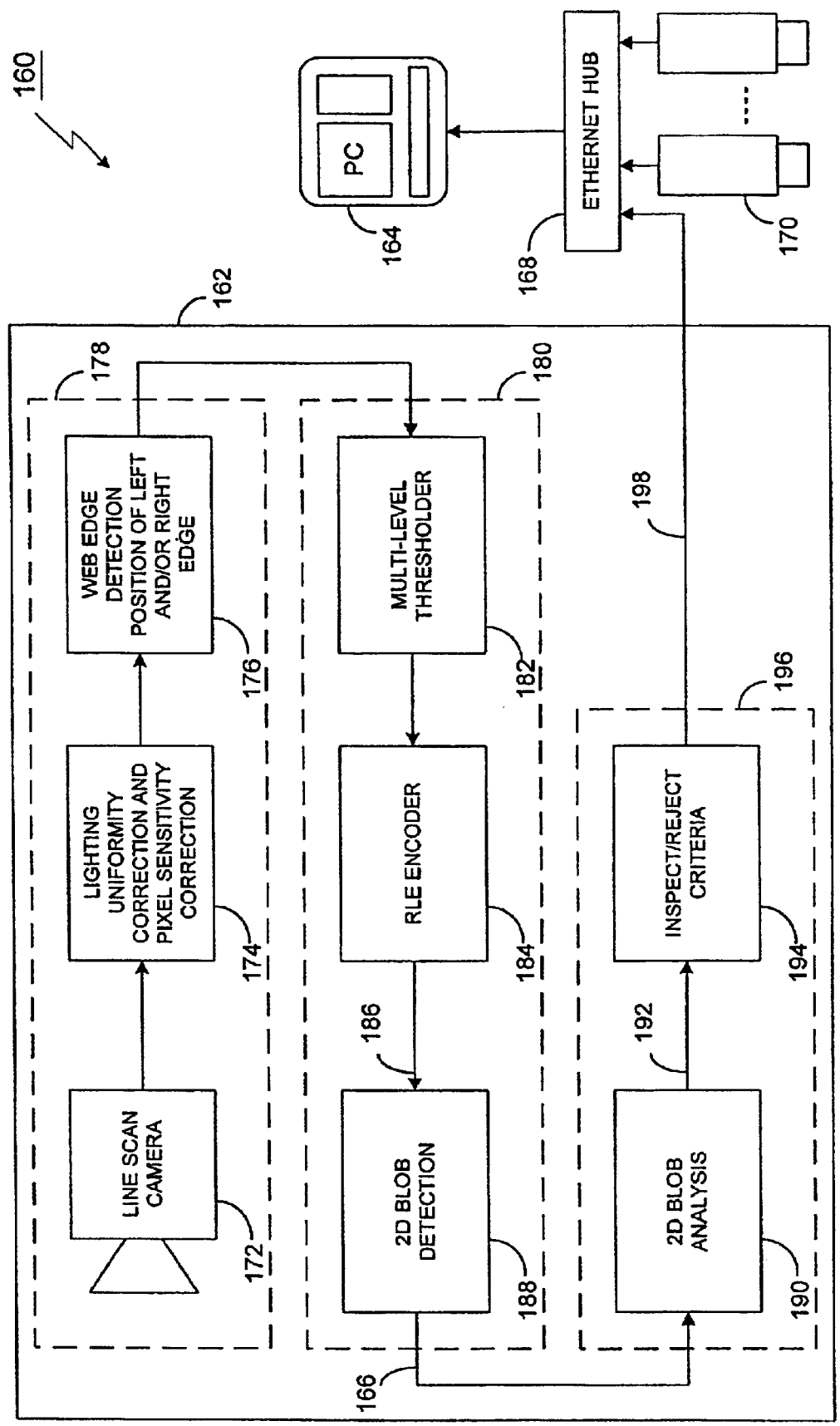
FIG. 4 is a block diagram of a high contrast web inspection system of the present invention.

FIG. 4 illustrates a block diagram of a high contrast web inspection system 160. High contrast cameras 162,170 are connected to a host computer 164 via an ethernet hub 168. The high contrast camera 162 includes a line scan camera 172 for capturing a web image. A pixel signal of the image is corrected for lighting uniformity and pixel sensitivity 174. Lighting and pixel gain and/or offset is performed on a pixel by pixel basis utilizing known baseline values of lighting uniformity and pixel sensitivity. Unlike prior art systems, the present invention performs the correction immediately upon obtaining the image such that the flaw detection algorithms are receiving corrected data.

Continuing with FIG. 4, the corrected signal is processed for web edge detection 176. Tracking of the edge(s) of web is very useful in order to distinguish between a web flaw or defect and a web edge. Web edges may not be even along the length of the web, or may vary in thickness, and texture, etc., and/or the web may drift along the cross direction. Any of these conditions may result in false flaw detection. Thus web edge detection 176 is programmable to allow for web edge variations in order to avoid detection of false flaws. Various methods of web edge detection may include tracking the web edge and/or processing images to a pre-determined position from the tracked edge. Thus, as the web drifts or the web width varies, the image detection area will also vary. In another method, web edges may be ignored by determining an image detection width that will always fall within a drift allowance. For web materials that require flawless edges, the web edge detection 176 may be programmed for exact tolerances. In addition, the web edge detection 176 may be bypassed completely if all potential flaw information is desired.

Continuing with FIG. 4, multi-level thresholding 182 is applied to the video signal received from the web edge detector 176. The multi-level thresholder 182 applies a compression technique on areas of the scanned image. Each line scan camera 172 scans an area of the web equal to a one pixel length by a pixel width in the cross direction of the web, which may be represented by a digital array. In a preferred embodiment, the multi-level thresholder 172 reduces the array to up to thirty-two groups of similar pixels. The multi-level thresholder 182 may be set to distinguish predetermined thresholds. For example, a grey scale having three groups may be utilized to categorize each pixel as acceptable, dark, and light.

The group information from the multi-level thresholder 172 is sent to a run length encoder ("RLE") 184 to generate data regarding the location of the pixels that are on the leading and the following edge of a group. For example, a first group that exceeds a threshold, as determined by the multi-level thresholder 172, may be identified as located on a first line number along the machine direction, and starting at pixel 1000 and ending at pixel 1010 along the cross direction. The RLE 184, which functions as a one dimensional blob detector, determines candidate areas for further processing, and does not make judgements as to whether a group is a flaw or a defect.

The RLE 184 transmits the multi-level thresholder groups pixel signal and informational data 186, including the group numbers, the line number, and the start and stop pixel numbers, to the two dimensional (2D) blob detector 188. The 2D blob detector 188 and the 2D blob analysis 190 perform a connectivity analysis on subsequent scanned lines in the machine direction to determine whether groups with the same class touch and form blobs, and whether a streak exists in the machine direction. In a preferred embodiment, the streak detection is performed in hardware in the 2D blob detector 188 because the streaks must be detected based upon adjacent pixels in the machine direction. The pixel signal and informational data 166 is sent to the 2D blob analysis 190 for further blob analysis performed in software. In other embodiments the division of responsibilities for analysis may vary between the 2D blob detector 188 and the 2D blob analyzer 190. In yet other embodiments of the present invention, the 2D blob detection and analysis function 188,190 may be combined.

In the preferred embodiment, as shown in FIG. 4, the linescan camera 172, the lighting uniformity correction and pixel sensitivity correction 174, and the web edge detection are preformed on a head board 178. The multi-level thresholder 182, the RLE encoder 184, and the 2D blob detection 188 are performed on a field programmable gate array ("FPGA") 180. The preferred embodiment utilizes flash memory to update the software or parameters such as the lighting correction coefficient. Software tasks such as 2D blob analysis 190 and inspect/reject analysis 194 are performed on a processor 196 inside of the smart camera 162.

Continuing with FIG. 4, 2D blob analysis data 192, including the bounding box data, the area, the length, the width and the aspect ratio, is analyzed according to a predetermined inspect/reject criteria 194 to determine whether each identified blob is a flaw or defect. The resulting data 198, including the position of the left and right edges of the web, and the bounding box, the area, the length, the width, the aspect ratio and the digitized image of the flaw are sent to the host computer 164 via the ethernet device 168.

In a preferred embodiment, the various connections between the host computer 164 and the cameras 162,170 i.e., the ethernet bandwidth allocation, are prioritized such that error and flaw feature data is given high priority and image data is given low priority. For example, the web inspection system 160 prioritizes marking a flaw on the web before showing an image of the flaw. If no or few flaws are detected on the web, then the bandwidth is available for other tasks such as to periodically transmit images of the good web product.

The high contrast web inspection system 160, as shown in FIG. 4, only utilizes a fixed threshold to classify individual pixels, e.g. gray scale pixels are compared to a threshold. However, when the contrast between good material and bad material is small, or if the web material has a large color variation, then the high contrast web inspection system 160 can no longer accurately and consistently detect flaws. For materials that have a tolerance range, such that the contrast of a flaw is relative to the surrounding background material as opposed to being an absolute value, a simple threshold evaluation can not be used. The medium contrast web inspection system 200 of FIG. 5 illustrates a system that can detect up to a two percent contrast difference.

Figure 5:
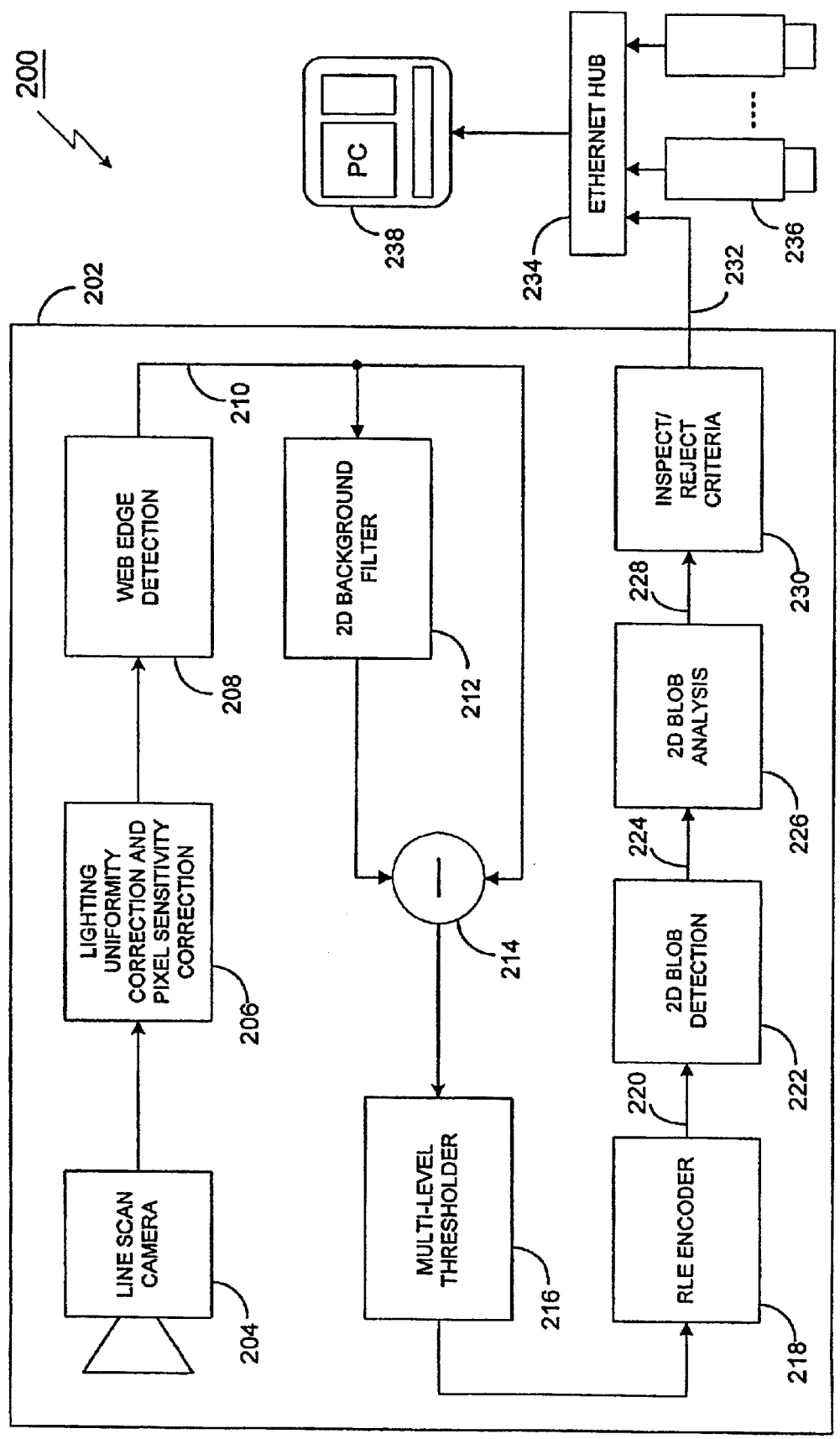
FIG. 5 is a block diagram of a medium contrast web inspection system of the present invention.

Referring to FIG. 5, similar to the high contrast smart camera 162 of FIG. 4, the medium contrast smart camera 202 includes a line scan camera 204, a lighting uniformity correction and pixel sensitivity correction 206, a web edge detector 208, a multi-level thresholder 216, an RLE encoder 218, a 2D blob detector and analyzer 222, 226 and an inspect/reject criteria 230. However, the medium contrast smart camera also includes a 2D background filter 212. The 2D background filter 212 takes an average that represents good product over a distance of the web along both the cross and the machine direction, sets the multi-level threshold 216 at a percent deviation of the good product average. The 2D background filter utilizes the pixel data 210 for a sequence of scan lines from the line scan camera 204, and calculates a running average. The average at any given point in time, i.e., along the length of the web, becomes a reference for good product for the a region local to that average. Thus, the medium contrast web inspection camera 162 is capable of adapting to changing characteristics of the web. In a preferred embodiment, the area analyzed by the 2D background filter is given by $2^n \times 2^m$, where n ranges from 0 to 8, and m ranges from 0 to 8. Thus, for n=0 or m=0, the 2D background filter is a two by two pixel area.

Continuing with FIG. 5, the 2D averaged signal is subtracted from the unfiltered signal 210 utilizing an adaptive background subtraction 214. In a preferred embodiment of the present invention, the 2D background filter 212 and adaptive back ground subtraction 214 are implemented in hardware, e.g. on a field programmable gate array. The filtered one dimensional video from the adaptive background subtraction 214 is sent to the multi-level thresholder 216 which groups the data for a scan line. In a preferred embodiment of the medium contrast web inspection camera 202, the multi-level thresholder utilizes up to 16 designation groups. Upon completion of the inspect/reject criteria analysis 230, the flaw classifications and statistics, flaw dimensions, and image data 232 is transmitted to the host computer 238 from each medium contrast camera 202, 236 via the ethernet hub 234.

Figure 6A:
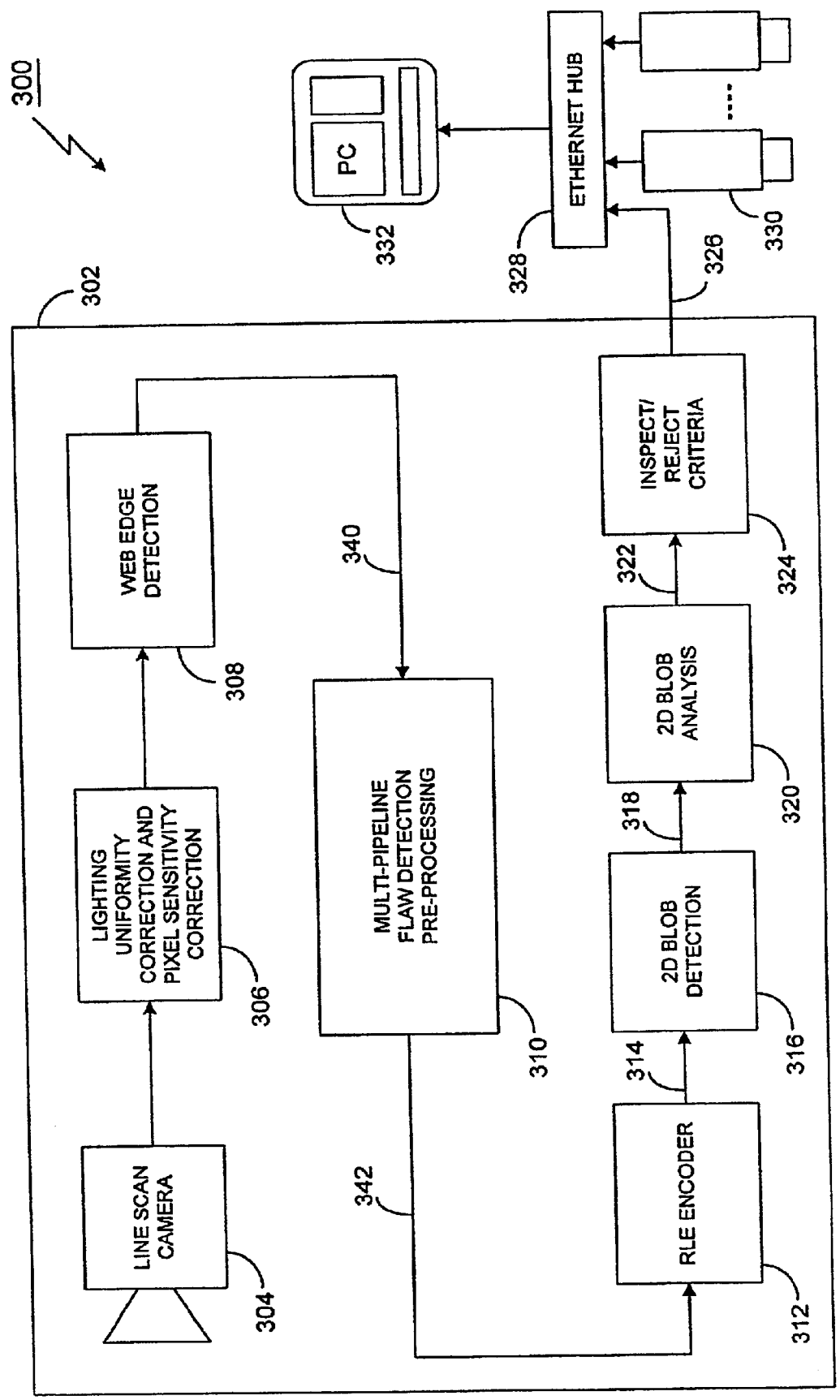
FIG. 6a is a block diagram of a low contrast web inspection system of the present invention.

FIG. 6A illustrates a low contrast web inspection system 300 of a preferred embodiment. The low contrast line scan cameras 302, 330 are capable of detecting a contrast between good web material and flawed web material that is very close to the noise level utilizing a multi-pipeline flaw detection pre-processor 310. A variety of filters used in conjugation with adaptive background subtraction, and a multiple of threshold detectors allow detection of very small changes in the web material. Materials requiring a low contrast detection include porous material and metallic surfaces.

Figure 6B:
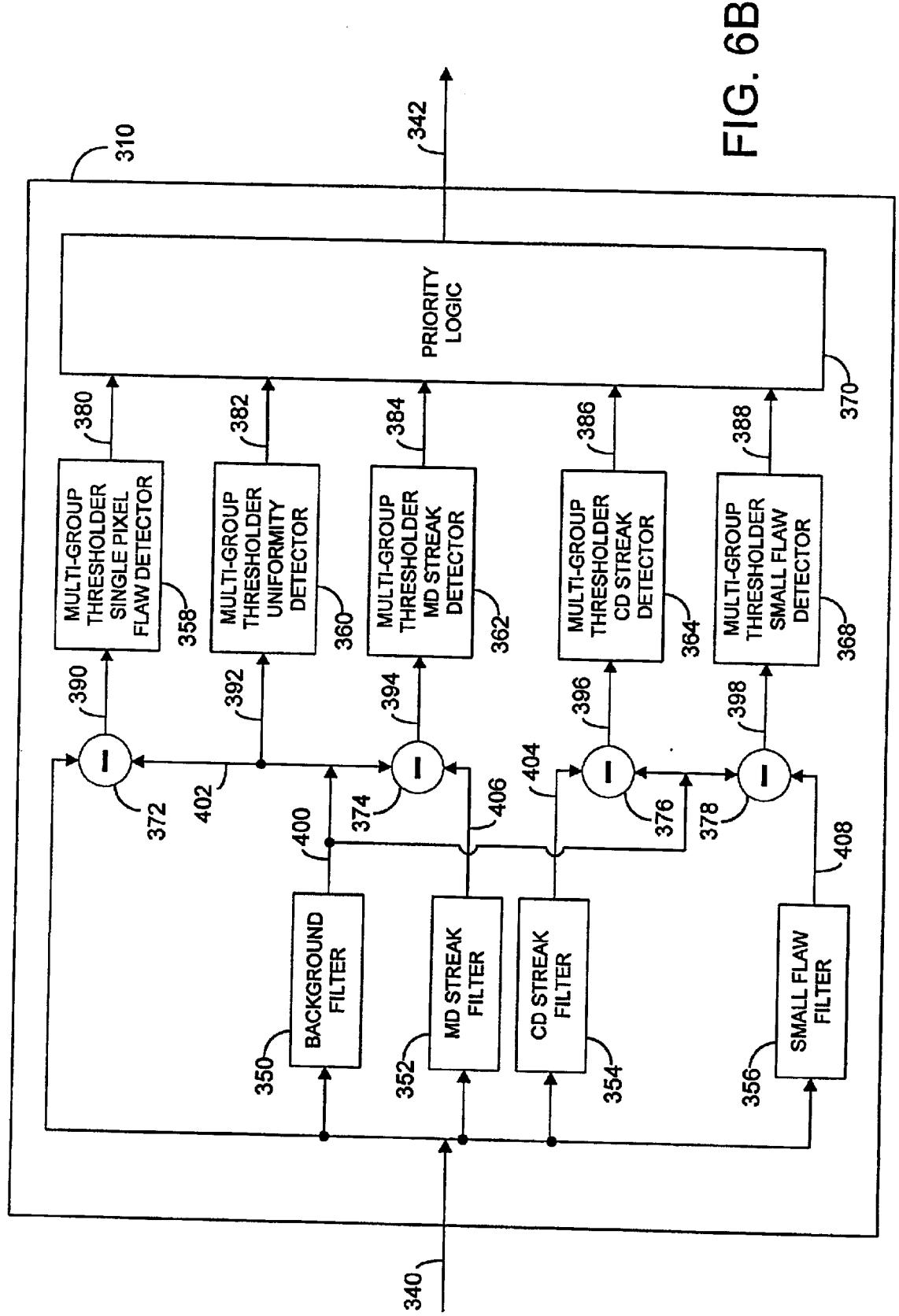

Continuing with FIG. 6A a line scan camera 304 produces digital pixel line scan data that is corrected for lighting uniformity and pixel sensitivity 306. The edge of the web is detected 308 and the corrected digital pixel line scan data and web edge data 340 are transmitted to a multi-pipeline flaw detection pre-processor 310. FIG. 6B is a block diagram of the pre-processor 310 of FIG. 6A. Four programmable 2D filters, including a background filter 350, a machine direction streak filter 352, a cross direction streak filter 354 and a small flaw filter 356 process the incoming corrected pixel line scan data 340. Each 2D filter 350, 352, 354, 356 utilizes the corrected pixel data 340 to calculate running averages along a length and width of the web. The averages 400, 404, 406, 408 become references for good product for regions local to each average. In a preferred embodiment of the present invention the area averaged by the 2D background filter 350 and the small flaw filter 356 is given by $2^a \times 2^b$, where "a" ranges from 0 to 11, and "b" ranges from 0 to 11. Thus, for $^a$=0 or $^b$=0, the 2D background filter or small flaw filter may be bypassed. In a preferred embodiment, the 2D MD streak filter 352 averages an area given by $2^a \times 2^b$, where "a" ranges from 0 to 11, and "b" ranges from 0 to 11. The 2D CD streak filter 354 averages an area given by $2^a \times 2^b$, where "a" ranges from 0 to 11, and "b" ranges from 0 to 11. Four adaptive background subtraction channels 372, 374, 376, 378 operate on the outputs of the filters by subtracting a portion 402 of the background filtered signal 400 from the corrected signal 340, the MD streak filtered signal 406, the CD streak filtered signal 404, and the small flaw filtered signal 408. In alternate embodiments of the present invention, the number of filters may vary.

Continuing with FIG. 6B, four multi-group thresholders 358, 362, 364, 368 group pixels for each output 390, 394, 396, 398 of the adaptive background subtraction channels 372, 374, 376, 378. A fifth multi-group thresholder 360 groups pixels for a portion 392 of the output signal 400 of the background filter 350. In a preferred embodiment, each multi-group thresholder 358, 360, 362, 364, 368 utilizes up to four groups. However, the number of threshold groups may vary according to specific applications as required. The output 380 of the single pixel flaw detector 358 may consist of single pixel errors such as holes. The output 382 of the uniformity detector 360 may consist of larger potential block flaws. The MD streak detector 362 and the CD Streak detector 364 detect narrow streaks in the machine direction and cross direction 384, 386, respectively. The small flaw detector 368 may be utilized to detect smaller potential block flaws 388. The multiple, multi-group thresholder detectors 358, 360, 362, 364, 368 supply a plurality of video streams that may contain flaws and defects. Thus, priority logic 370 is utilized to apply thresholds and rules to the video streams 380, 382, 384, 386, 388.

Referring back to FIG. 6a, the RLE encoder 312 generates start-stop pixel information for the detected prioritized flaws and defects 342, and sends the video stream and start-stop data 314 to the 2D blob detector 316. Upon completion of the 2D blob detection 316, 2D blob analysis 320, and the inspect/reject criteria analysis 324, the flaw classifications and statistics, flaw dimensions, and image data 326 is transmitted to the host computer 332 from each low contrast camera 302, 330 via the ethernet hub 328.

Figure 7:
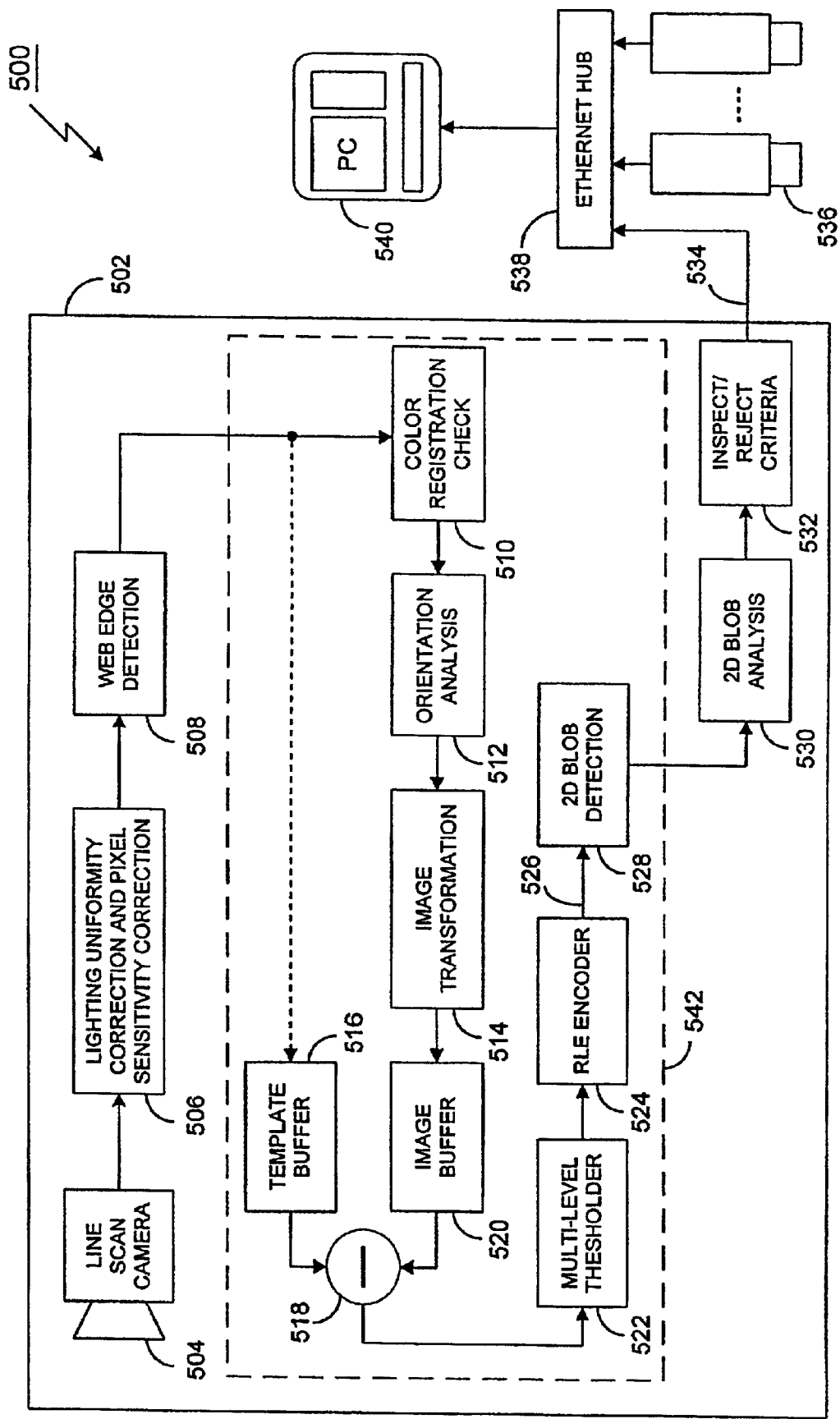
FIG. 7 is a block diagram of a print web inspection system.

FIG. 7 illustrates a preferred embodiment of a print web inspection system 500 for detecting flaws and defects in printed webs. The print consists of discrete patterns applied by techniques such as offset printing, flexo-graphic printing. Applications are pharmaceutical label verification, poster board inspection, box inspection, and plastic bag inspection. Flaw detection is based upon template matching. As shown in the print web smart camera 502 of FIG. 7, the video stream from a line scan camera 504 is lighting and pixel corrected 506 on a pixel by pixel basis. The edge of the web is detected 508 and the pixel and related data is input to a preprocessing pipeline 542. In a preferred embodiment, the web is checked for color registration 510. An orientation analysis 512 is performed for a new pattern based upon translation, rotation and stretch. Thus, if a web skews or stretches, software or hardware in the print web camera 502 can compensate for the distortion. The image is transformed 514 to fit a golden template. A subtraction channel 518 subtracts the web image output of an image buffer 520 from an image in a template buffer 516. The resulting pixel stream is grouped in a multi-level thresholder 522, and RLE encoded 524. A 2D blob detection 528 and a 2D blob analysis 530 is performed on the grouped data 526. The results of the analysis are inspected based upon predetermined reject criteria 532. The resulting inspect/reject flaw analysis, flaw classification and statistics, flaw dimensions and image data 534 are transmitted via an ethernet hub 538 to a host computer 540. The host computer 540 then process the data and image streams from all of the print inspection cameras 502, 536 that are connected to the ethernet 538.

Figure 8:
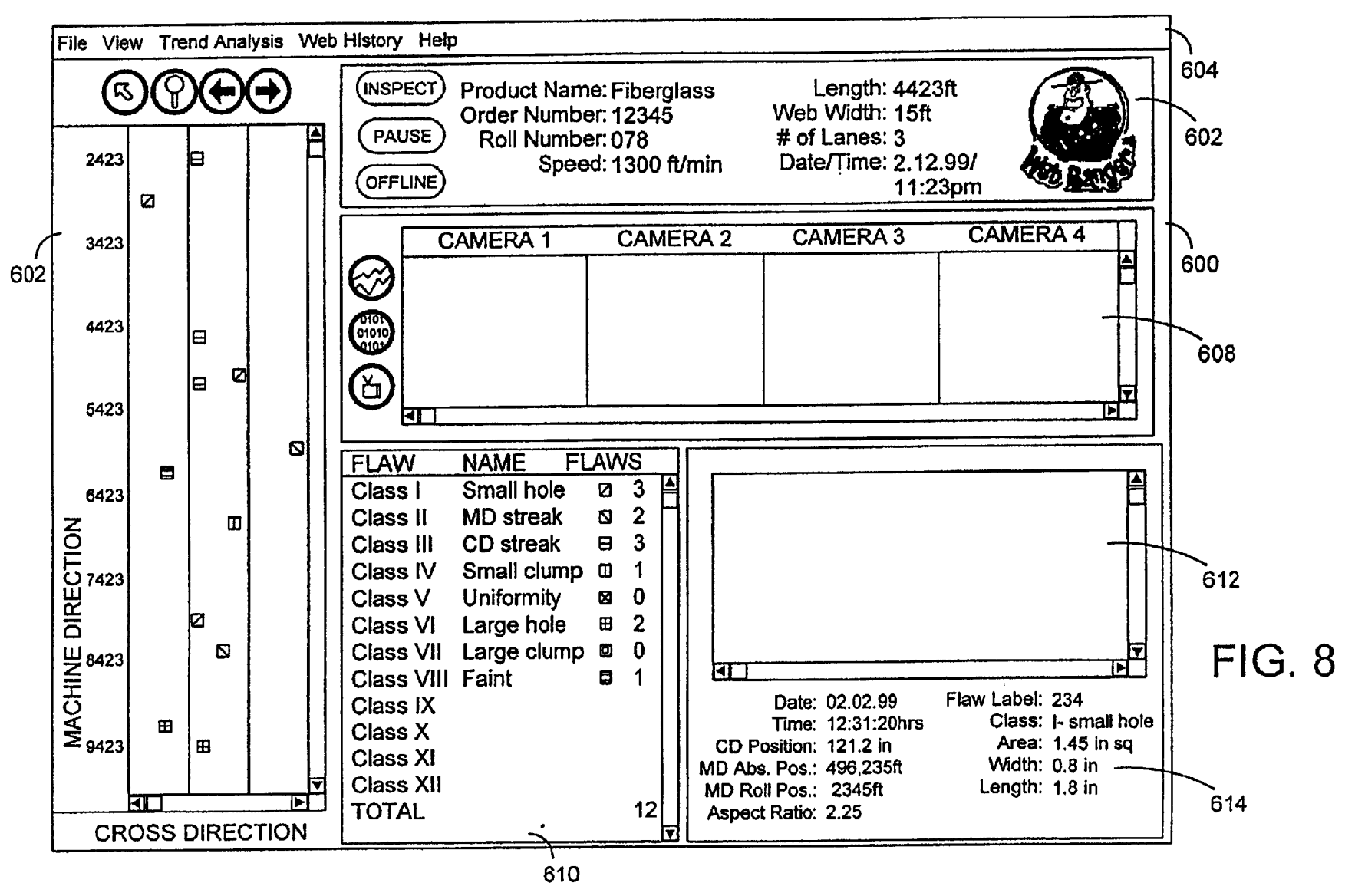

FIG. 8 illustrates the graphical user interface 600 ("GUI") for the monitoring software of an online web inspection system of a preferred embodiment as shown in FIGS. 6A and 6B. The GUI includes a pull-down menu bar 604 that provides access to stored files for web inspections, trend analysis, and web histories. A web map window 602 displays representations of the detected flaws in a machine and cross direction per a legend 610. A flaw window 612 shows a specific detected flaw as identified by the flaw information 614 below the flaw window 612. A camera web window 608 shows an image of the moving web for each camera in the inspection system. Web data statistics 602 are displayed for the current web.

The trend analysis, available as an option on the menu tool bar 604, analyzes the detected flaws and defects by cross direction and frequency. Thus, if a particular flaw appears in the same cross direction position at regular machine direction intervals, then the monitoring software alerts the operator of a potential problem occurring on the web manufacturing line. The availability of the automatic trend analysis may permit root cause analysis, allowing diagnosis and elimination of flaw-producing mechanisms, resulting in significant savings to the web manufacturer.

Figure 9:
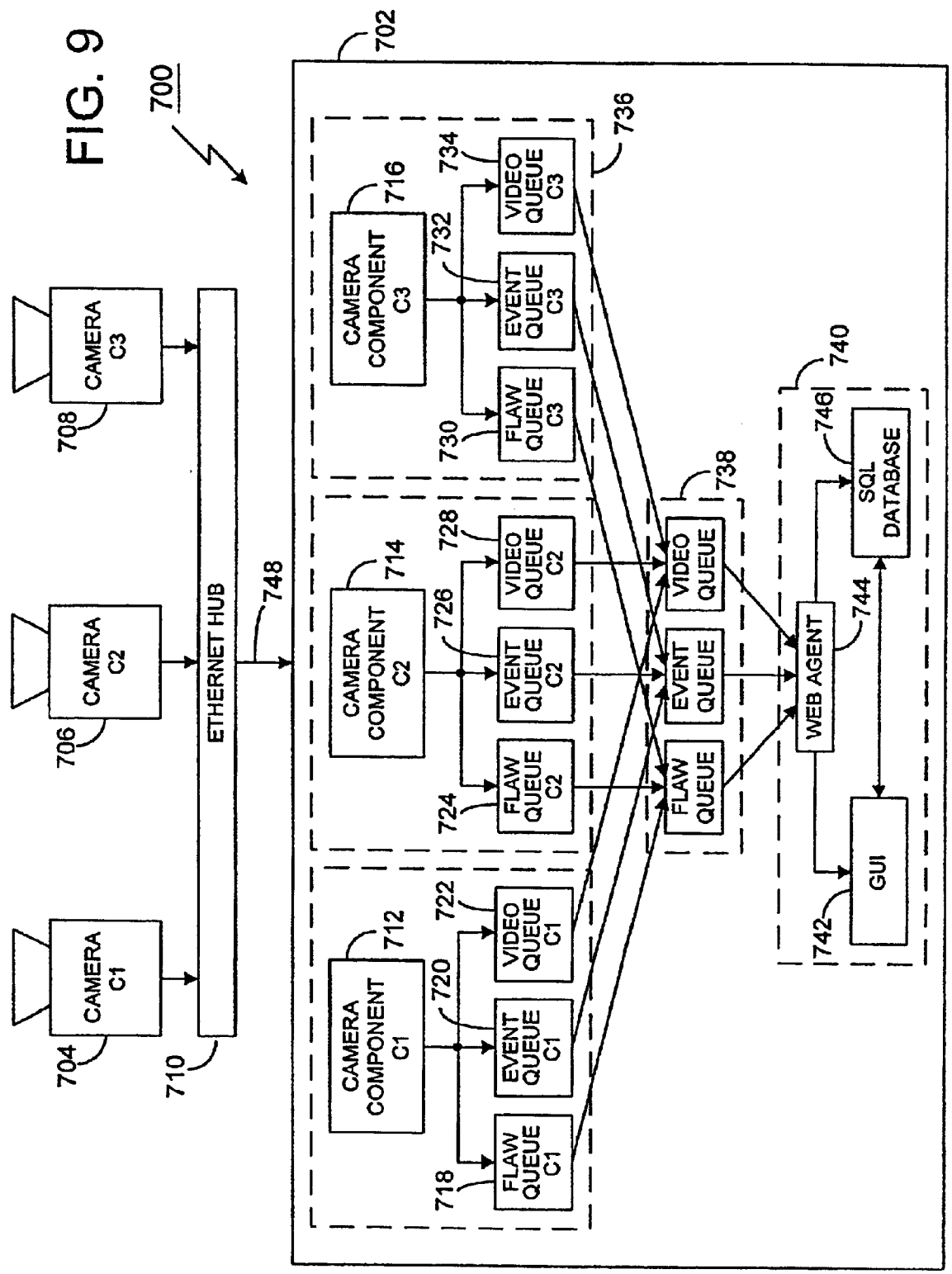
FIG. 9 is an illustration of the web system software architecture of the present invention.

FIG. 9 illustrates a host computer software architecture 702 for a web inspection system 700 of a preferred embodiment of the present invention. Three smart cameras 704, 706, 708 are connected to an ethernet hub 710 and transmitted 748 to the host computer 702. For ease of illustration, only three smart cameras are shown. However, the preferred embodiment may include any number of smart cameras, as required. Continuing with FIG. 9, each camera 704, 706, 708 sends video and data to a corresponding software block 736. Camera C1 704 is represented in software by a camera component 712 which generates a flaw queue C1 718, and event queue C1 720, and a video queue C1 722. Camera C2 706 is represented in software by a camera component 714 which generates a flaw queue C2 724, and event queue C2 726, and a video queue C2 728. Similarly, camera C3 708 is represented in software by a camera component 716 which generates a flaw queue C3 730, and event queue C3 732, and a video queue C3 734.

A multi-camera component 738 ("MCC") combines information from each camera component 712, 714, 716 to form a single flaw queue, event queue and video queue. The multi-camera component 738 sends the queue information to a controller 740. The video queue includes detected flaw image data as well as good web image data when permitted by bandwidth availability. The flaw queue includes flaw information such as the location and type of detected flaws. The event queue includes other signals received by host computer including printer on or off signals, a "cut" signal from web, operator input, and status changes. A web agent 744 sends the flaw, event and video queue data to appropriate devices such as the graphical user interface 742. An SQL database 746 is available to receive and send information from/to the graphical user interface 742.

Although a preferred embodiment of the invention has been described above by way of example only, it will be understood by those skilled in the field that modifications may be made to the disclosed embodiment without departing from the scope of the invention, which is defined by the appended claims.

We claim:

1. A web inspection system for detecting a plurality of web flaws of a web, the web inspection system comprising:

a plurality of smart cameras for generating a digital pixel representation of a portion of the web, each smart camera for detecting the plurality of web flaws from the digital pixel representation and for generating output data comprising a digitized image of each flaw of the plurality of web flaws and for generating flaw location data for each flaw of the plurality of web flaws;

a host computer for controlling the web inspection system and for receiving and displaying the flaw image data and the flaw location data; and an ethernet for connecting the plurality of smart cameras to the host computer, wherein the flaw image data and the flaw location data is transmitted over the ethernet from the plurality of smart cameras to the host computer, each smart camera of the plurality of smart cameras comprises:

a line scan camera for generating the digital pixel representation of a portion of the web;

a lighting uniformity and pixel sensitivity correction means for correcting each pixel of the digital pixel representation and for providing a corrected pixel representation;

a web edge detector for detecting at least one edge of the web;

a multi-pipeline pre-processor for filtering the corrected pixel representation, the multi-pipeline pre-processor generating a prioritized data stream of potential flaws;

a run length encoder for generating location data regarding a location of each group of the potential flaws in a cross direction;

a blob detector for generating block data regarding the location of blocks of the potential flaws along a machine direction; and an inspect/reject analyzer for determining actual flaw data from the prioritized data stream of potential flaws.

2. The web inspection system of claim 1, wherein the multi-pipeline processor comprises:

a plurality of filters for averaging the corrected pixel representation over a distance of the web along a machine direction of the web;

a plurality of adaptive background subtraction channels connected to the plurality of filters, each adaptive background subtraction channel of the plurality of adaptive background subtraction channels producing a stream of subtracted pixel representations;

a plurality of thresholders, each thresholder of the plurality of thresholders connected to an output of an adaptive background subtraction channel of the plurality of adaptive background subtraction channels, each thresholder for grouping at least a portion of the stream of subtracted pixel representations and for producing a thresholder group output; and a priority logic circuit for prioritizing the thresholder group output of each of the plurality of thresholders.

3. The web inspection system of claim 2, wherein the plurality of filters comprises:

a background filter;

a machine direction streak filter;

a cross direction streak filter; and a small flaw filter.

4. The web inspection system of claim 2, wherein the plurality of thresholders comprises:

a single pixel flaw detector;

a uniformity detector;

a machine direction streak detector;

a cross direction streak detector; and a small flaw detector.

5. The web inspection system of claim 1, wherein each smart camera of the plurality of smart cameras detects the plurality of web flaws from the digital pixel representation at a contrast approaching a signal noise level.

6. A method of low contrast web inspection of a web, the method comprising the steps of:

providing at least one smart camera for detecting at least one flaw on the web, wherein detecting the at least one flaw on the web comprises the steps of:

generating flaw image data of the at least one flaw, the flaw image data comprising an area of pixels having a length and a width;

generating flaw location data for locating the at least one flaw on the web; and transmitting the flaw image data and flaw location data over an ethernet to a host computer; and displaying the flaw image data and flaw location data on the host computer; and wherein the step of generating the flaw image data and flaw location data comprises the steps of:

generating a pixel representation of the at least a portion of the web;

correcting the pixel representation for a lighting uniformity and a pixel sensitivity;

filtering the corrected pixel representation utilizing a plurality of filters;

grouping the filtered corrected pixel representations to generate a plurality of potential flaw data streams;

generating a prioritized data stream from the plurality of potential flaw data streams;

generating cross direction location data regarding a location of the prioritized data stream;

generating block data regarding the location of blocks of the prioritized data stream along a machine direction; and generating the flaw image data from the prioritized data stream of potential flaws utilizing the cross direction location data and the block data.

7. A web inspection system for detecting a flaw of a plurality of possible flaws on a web, the web inspection system comprising:

at least one smart camera for generating a digitized video data stream of a flaw on a portion of the web, the at least one smart camera comprising:

a background filter for averaging the digitized video data stream over a first area of the web to generate an averaged background signal;

a machine direction streak filter for averaging the digitized video data stream over a distance of the web along a machine direction of the web to generate a filtered machine direction signal;

a cross direction streak filter for averaging the digitized video data stream over a distance of the web along a cross direction of the web to generate a filtered cross direction signal;

a first adaptive background subtraction channel for subtracting the averaged background signal from the filtered machine direction signal to generate a first pixel representation;

a second adaptive background subtraction channel for subtracting the averaged background signal from the filtered cross direction signal to generate a second pixel representation;

at least one multi-group thresholder for grouping the first and second pixel representations to generate at least two data streams of potential flaws; and a priority logic circuit for prioritizing the at least two data streams of potential flaws to generate the digitized video data stream of the flaw.

8. The web inspection system of claim 7, wherein the at least one multi-group thresholder comprises:

a machine direction streak detector for detecting a narrow streak in the machine direction; and a cross direction streak detector for detecting a narrow streak in the cross direction.

9. The web inspection system of claim 7, further comprising:

a small flaw filter for averaging the digitized video data stream over a second area of the web to generate an averaged small flaw signal; and a third adaptive background subtraction channel for subtracting the averaged background signal from the average small flaw signal to generate a third pixel representation; and a small flaw detector for detecting a small block flaw from the third pixel representation.

10. The web inspection system of claim 7, further comprising a single pixel adaptive background subtraction channel for subtracting the averaged background signal from the digitized video data stream, an output of the single pixel adaptive background subtraction channel coupled to a single pixel flaw detector having an output of single pixel flaws.

11. The web inspection system of claim 7, further comprising a uniformity detector having an input of the averaged background signal, the uniformity detector for outputting a block flaw signal.

* * * * *